(12) United States Patent
Sullivan (10) Patent No.: US 7,691,046 B2
(45) Date of Patent: Apr. 6, 2010

(54) NONDESTRUCTIVE FLUID TRANSFER DEVICE

(75) Inventor: Paul J. Sullivan, Plymouth, MN (US)

(73) Assignee: PumpWorks, Inc., Minneapolis, MN (US)

( * ) Notice: Subject to any disclaimer, the term of this patent is extended or adjusted under 35 U.S.C. 154(b) by 22 days.

(21) Appl. No.: 11/482,791

(22) Filed: Jul. 10, 2006

(65) Prior Publication Data

US 2006/0252977 A1     Nov. 9, 2006

Related U.S. Application Data

(63) Continuation of application No. PCT/US2005/000477, filed on Jan. 10, 2005.

(60) Provisional application No. 60/534,685, filed on Jan. 8, 2004.

(51) Int. Cl.
*A61M 1/12* (2006.01)
(52) U.S. Cl. .......................................... 600/16
(58) Field of Classification Search .................. 600/16, 600/17
See application file for complete search history.

(56) References Cited

U.S. PATENT DOCUMENTS

| | | | |
|---|---|---|---|
| 3,608,088 A | 9/1971 | Dorman et al. | |
| 3,831,203 A | 8/1974 | Ridgway | |
| 3,955,557 A | * 5/1976 | Takagi | 600/16 |
| 4,034,742 A | 7/1977 | Thoma | |
| 4,144,595 A | 3/1979 | Unger | |
| 4,222,127 A | 9/1980 | Donachy et al. | |
| 4,250,872 A | 2/1981 | Tamari | |
| 4,573,997 A | 3/1986 | Wisman et al. | |
| 4,690,134 A | 9/1987 | Snyders | |
| 4,902,291 A | 2/1990 | Kolff | |

(Continued)

FOREIGN PATENT DOCUMENTS

WO     WO 95/18593     7/1995

(Continued)

OTHER PUBLICATIONS

The VAD Heart Pump (Engineering the Pulse of Life), The Whitaker Foundation 2001 Annual Report, p. 12 (2001).

(Continued)

*Primary Examiner*—Carl H. Layno
*Assistant Examiner*—Jon-Eric C. Morales
(74) *Attorney, Agent, or Firm*—Patterson, Thuente, Skaar & Christensen, P.A.

(57) ABSTRACT

Fluid transfer device configured as a vacuum pump particularly suited for nondestructive transfer of fluids, including blood and blood constituents. Fluid transfer device used for assisting in the pumping of blood through a patient's heart for reducing the load on the heart, reducing forces and blood pressure on the inner walls of the heart is reduced. Examples are aortic assist device, a ventricular assist device, or artificial heart. Industrial applications include the pumping of fluids, including destructible fluids such as foodstuff with or without food constituents of various sizes within the foodstuff. Food and other fluids may be stored until they are dispensed. By use of a vacuum, the device is operated at no more than atmospheric pressure. A pre-charged pressure tank may be used, such as where fluid pressure of the pumped fluid, including backpressure of body fluids, where pressure greater than atmospheric is required to expel pumped fluid.

19 Claims, 9 Drawing Sheets

U.S. PATENT DOCUMENTS

| | | | |
|---|---|---|---|
| 4,925,443 A * | 5/1990 | Heilman et al. ............... | 600/16 |
| 4,938,766 A | 7/1990 | Jarvik | |
| 5,089,016 A | 2/1992 | Millner et al. | |
| 5,192,314 A | 3/1993 | Daskalakis | |
| 5,282,849 A | 2/1994 | Kolff et al. | |
| 5,453,076 A | 9/1995 | Kiyota et al. | |
| 5,707,336 A | 1/1998 | Rubin | |
| 5,728,069 A | 3/1998 | Montevecchi et al. | |
| 5,899,937 A | 5/1999 | Goldstein et al. | |
| 5,910,124 A | 6/1999 | Rubin | |
| 6,579,223 B2 | 6/2003 | Palmer | |
| 2004/0054251 A1 | 3/2004 | Liotta | |

FOREIGN PATENT DOCUMENTS

| | | |
|---|---|---|
| WO | WO 00/25842 | 5/2000 |
| WO | WO 2005/070477 A1 | 8/2005 |

OTHER PUBLICATIONS

Hager, Larrie, First U.S. Child Receives Implanted Miniature Heart Pump at UMHS, University of Michigan Health System, (Press Release) (Feb. 14, 2003), 2 pages.

The Methodist Hospital and Baylor College of Medicine Surgeons Implant First U.S. Patient with MicroMed DeBakey Ventricular Assist Device™, PR Newswire (Jan. 8, 2000), 1 page.

Bluck, John, NASA Computer Science Helps Heart Pump Team win Invention of the Year, NASA Ames Research Center, (Press Release) (Apr. 2, 2002), 2 pages.

Darwin, Jennifer; Heart Device Breakthroughs Beating Strong in Houston, Houston Business Journal (Apr. 28, 2000), 4 pages.

Darwin Dawson, Jennifer; Investor Groups Pump $23 million Into MicroMed Technology, Houston Business Journal (Oct. 4, 2002), 3 pages.

CHF Patients.com—LVADS (Heart Pumps), Updated (Nov. 27, 2005), available at: http://www.chfpatients.com/implants/lvads.htm, 11 pages.

Thoratec Ventricular Assist Device (VAD), Texas Heart Institute at St. Luke's Episcopal Hospital (Oct. 18, 2006), available at: http://www.texasheart.org/Research/Devices/thoratec.cfm, 2 pages.

Surgery and Devices for Congestive Heart Failure, MyHeartCentral.com (Apr. 11, 2006), available at: http://www.heathcentral.com/heart-disease/surviving-heart-attack-000013_9-145_pf.html, 6 pages.

New Device Gives Heart Failure Patients More Freedom, The University of Chicago Medical Center (Oct. 30, 2000), 4 pages.

Lifesaving TandemHeart™ Used for First Time in U.S.; Revolutionizes Heart Treatment, Texas Heart Institute at St. Luke's Episcopal Hospital, PR Newswire (Oct. 24, 2000), 3 pages.

AbioMed AB5000, Texas Heart Institute at St. Luke's Episcopal Hospital, available at: http://www.texasheart.org/Research/Devices/abiomed_ab5000.cfm, Heart Assist Devices (Oct. 18, 2006), 1 page.

AbioMed BVS 5000, Texas Heart Institute at St. Luke's Episcopal Hospital, available at: http://www.texasheart.org/Research/Devices/abiomed_ab5000.cfm (Oct. 18, 2006), 2 pages.

Intra-Aortic Balloon Pump, Texas Heart Institute at St. Luke's Episcopal Hospital, available at: http://www.texasheart.org/Research/Devices/index.cfm (Oct. 18, 2006), 2 pages.

AbioCor Implantable, Texas Heart Institute at St. Luke's Episcopal Hospital, available at: http://www.texasheart.org/Research/Devices/index.cfm (Aug. 19, 2006), 2 pages.

Levitronix CentriMag LVAS, Texas Heart Institute at St. Luke's Episcopal Hospital, available at: http://www.texasheart.org/Research/Devices/levitronix.cfm (Oct. 18, 2006), 1 page.

Medtronic Bio-Pump, Texas Heart Institute at St. Luke's Episcopal Hospital, available at: http://www.texasheart.org/Research/Devices/biopump.cfm (Oct. 18, 2006), 2 pages.

TandemHeart pVAD, Texas Heart Institute at St. Luke's Episcopal Hospital, available at: http://www.texasheart.org/Research/Devices/tandemheart.cfm (Oct. 18, 2006), 2 pages.

Thoratec HeartMate II LVAS, Texas Heart Institute at St. Luke's Episcopal Hospital, available at: http://www.texasheart.org/Research/Devices/thoratec_heartmateii.cfm (Oct. 18, 2006), 2 pages.

Thoratec HeartMate IP LVAS, Texas Heart Institute at St. Luke's Episcopal Hospital, available at: http://www.texasheart.org/Research/Devices/heartip.cfm (Oct. 18, 2006), 1 page.

Thoratec HeartMate XVE LVAS, Texas Heart Institute at St. Luke's Episcopal Hospital, available at: http://www.texasheart.org/Research/Devices/heartve.cfm (Aug. 19, 2006), 1 page.

Thoratec VAD, Texas Heart Institute at St. Luke's Episcopal Hospital, available at: http://www.texasheart.org/Research/Devices/thoratec.cfm (Oct. 18, 2006), 1 page.

Jarvik 2000 Heart, Texas Heart Institute at St. Luke's Episcopal Hospital, available at: http://www.texasheart.org/Research/Devices/j2000.cfm (Aug. 19, 2006), 1 page.

* cited by examiner

NONDESTRUCTIVE FLUID TRANSFER DEVICE

CROSS-REFERENCE TO RELATED APPLICATIONS

This application is a continuation of application no. PCT/US2005/00477, filed Jan. 10, 2005, which claims the convention priority of U.S. patent application No. 60/534,685, filed Jan. 8, 2004, and each of which is incorporated herein by reference.

FIELD OF THE INVENTION

The invention relates to fluid transfer devices. More particularly, the invention relates to nondestructive fluid transfer devices. Even more particularly, the invention relates to fluid transfer devices particularly suited for use in medical applications, such as in the pumping of blood.

BACKGROUND OF THE INVENTION

Fluid transfer devices such as pumps are known.

Artificial heart assistance devices, such as ventricular assist devices (VADs) that draw blood from one of the ventricles of the heart and push the blood through the aorta are known.

Known devices have proven unsatisfactory for pumping blood and other easily damaged fluids.

Known cardiac assist devices have many drawbacks related to the particular requirements of pumping blood, useful life, and so forth.

OBJECTS AND SUMMARY OF THE INVENTION

It is an object of the invention to overcome the drawbacks of known devices.

A further object of the invention is to provide a fluid transfer device, such as a pump, usable for pumping fluids, such as liquids and gases.

A further object of the invention is to provide a fluid transfer device, such as a pump, usable for pumping destructible fluids, such as blood.

Another object of the invention is to provide a fluid transfer device which may be used internally or externally for assisting the heart.

A further object of the invention is to provide a nonshearing fluid transfer device, such as a pump.

A further object of the invention is to provide a fluid transfer device such as a pump, which may be used for pumping any destructible fluid, including viscous, semi-solid, and other fluids, including foodstuffs, such as salsa or chunky spaghetti sauce for which the user wants to maintain the integrity of the larger chunks of food, as well as condiments, or the dispensing of non-food product, such as soaps and shampoos, as the marketplace demands.

Yet another object of the invention is to provide a fluid transfer device which stores products until such time as the product is to be dispensed, such as for the dispensing of food, and other products, whether or not such products are readily degraded.

A still further object of the invention is to provide a fluid transfer device such as a pump, which inherently automatically continually cleans itself, in use.

A further object of the invention is to provide a fluid transfer device configured for pumping blood that automatically cleans itself.

A further object of the invention is to provide a medical pump which may be controlled by conventional pacemaker controls, in the case where the medical pump is used to assist the heart.

A still further object of the invention is to provide a fluid transfer device which may be used as a cardiac assist device, such as an aortic assist device or ventricular assist device (VAD), with or without the addition of one or more artificial heart valves.

Yet another object of the invention is to provide a fluid pump which may be used with an additional pump and requisite valving, power source, and controls to serve as an artificial heart.

Yet another object of the invention is to provide a medical device for transferring or pumping blood that has no entrapment areas, dead zones, or quiescent points that may lead to clotting and/or shearing of platelets and/or red blood cells (RBCs), for example, as in known devices.

A still further object of the invention is to provide a fluid transfer device, such as a pump, which avoids cross-fluid transfer or contamination.

A still further object of the invention is to provide a pump which prevents the evacuation of pressurized gas into the fluid being pumped.

Yet another object of the invention is to provide a pump which has a fail-safe mode selected to avoid destruction of the system in which the pump operates.

Another object of the invention is to provide a cardiac assist device which does not hamper heart blood flow in the case where the cardiac assist device suffers a loss of power.

Yet another object of the invention is to provide a cardiac assist device configured so that if a leak develops then a signal is sent to the user and/or the operation of the cardiac assist device is altered.

Another object of the invention is to provide a cardiac assist device configured so that in the event the cardiac assist device operation is altered or stops pumping blood (such as in the case of a power failure), less clotting of blood occurs than in known devices.

A further object of the invention is to provide a cardiac assist device configured so that sufficiently little clotting of a patient's blood occurs so as to enable the reduction or elimination of the patient's use of antiplatelet agents and/or anticoagulants than required by the use of known devices.

Another object of the invention is to provide a blood pump, such as a cardiac assist device, or an artificial heart, which causes little or no degradation of constituents of the blood being pumped.

Still another object of the invention is to provide a blood pumping device, such as a cardiac assist device, which substantially completely refreshes the volume of pumped blood and retains sufficiently little unpumped blood in its stopped or non-pumping state, so that there is substantially no accumulation of blood within the blood pump; i.e., blood which is not continually refreshed.

A further object of the invention is to provide a blood pump configured for minimizing the surface area of the pumping mechanism in contact with the blood being pumped, so as to minimize the surface area on which platelet accumulation and clotting may occur.

Another object of the invention is to provide a blood pump, such as a cardiac assist device, including a pumping element configured and selected so that a predetermined platelet accumulations occurs on a surface of the pumping device in contact with the blood being pumped, the predetermined accumulation being selected so as to prevent an undesirable excess accumulation of platelets which may lead to undesirable clotting of the blood being pumped.

A further object of the invention is to provide a blood pump which minimizes the volume of stagnant blood remaining in the pumping element of the pump during a non-pumping stage of a pumping cycle; i.e. a device which minimizes an unpumped volume resident in the blood pumping element of the blood pump.

Yet another object of the invention is to provide a cardiac assist device which requires no pacemaker.

Another object of the invention is to provide a cardiac assist device including one or more sensors capable of detecting one or both of the influx and outflow of blood into a ventricle of a heart, and/or the increase and decrease of the fluid pressure exerted by the blood in the heart to which it is connected; the detection by such sensor(s) being used to operate the cardiac assist device without an auxiliary control, such as a pacemaker.

Another object of the invention is to provide a method of implanting a cardiac assist device, such as an aortic or ventricular assist device, completely within a patient's torso or chest and, indeed, without the splitting of the sternum.

A further object of the invention is to provide a method of implanting a cardiac device, such as an artificial heart, completely within a patient's torso or chest.

Another object of the invention is to provide a cardiac assist device including a pumping element, such as a bladder, which includes a coating or layer or sensor adjacent the bladder and configured and selected so as to detect a fluid leak.

Another object of the invention is to minimize gas permeation into blood being pumped, as occurred in prior art gas-filled systems, the reduction of the likelihood of gas permeation being accomplished by, for example, the use of a negative pressure (e.g., the development of a vacuum) to draw in blood to be pumped, and the use of fluid at atmospheric pressure to pump out blood into the interior of the heart.

Another object of the invention is to provide a blood pump, such as a cardiac assist device, which reduces infection, thanks to its being fully implantable.

A further object of the invention is to provide a blood pump, such as a cardiac assist device, which may be configured for use in smaller patients, such as infants and preadolescents.

Another object of the invention is to provide a blood pump, such as a cardiac assist device, which may have a variable pumping rate and volume, which variable pumping rate and volume may be adjusted from outside the patient's body, so that, as an adult patient recovers, or as a child grows, for example, the pumping rate and volume may be increased, thereby eliminating the need to implant a new, larger device, as had been the case in the prior art.

Another object of the invention is to provide a blood pump, such as a cardiac assist device, having sufficiently low energy requirements that it may be operated by transformer coupled charging through the patient's skin.

A further object of the invention is to provide a blood pump, such as a cardiac assist device, which requires no percutaneous transfer of fluid energy or electrical energy in order to operate.

Yet another object of the invention is to provide a blood pump, such as a cardiac assist device, which includes a pulsatile pump, including a pulsatile pump with a variable pulsing rate.

A further object of the invention is to provide a blood pump, such as a cardiac assist device, in which one or both of the pumped fluid volume and the pumped fluid pressure may be varied.

Another object of the invention is to provide a blood pump, such as a cardiac assist device, which may be controlled by an implanted pacemaker inside or outside of the cardiac assist device housing and/or by pressure sensors configured for sensing blood pressure within a patient's heart, which pressure sensors may be provided inside or outside the housing of the cardiac assist device.

Another object of the invention is to provide a blood pump, such as a cardiac assist device, which includes an atmospheric pressure sensor, so that the pressure exerted by the pump may be varied to be substantially the same as atmospheric pressure to account for variations in atmospheric pressure, such as when the patient moves to a higher altitude.

Yet another object of the invention is to provide a blood pump, such as a cardiac assist device, which sufficiently minimizes stagnant blood contained within the pumping element of the device that no valve is required between the pumping element and the inside portion of the patient's heart to which the pumping device is fluidly connected.

Yet another object of the invention is to provide a blood pump which may be fluidly connected to one or more of the interior regions of a patient's heart, including, for example, the right ventricle, the left ventricle, the aorta, and so forth.

In summary, the invention includes an expandable expansion chamber, a hole or fluid connection provided in the expansion chamber, and a power unit operably associated with the expansion chamber for expanding the expansion chamber sufficiently to cause a fluid to be drawn into the expansion chamber through the hole or fluid connection.

The invention may likewise include an expansion chamber made of an elastic material.

The expansion chamber may be configured so that it has a normally unexpanded state; i.e. in its relaxed mode, it is in an unexpanded condition.

The power unit for expanding the expansion chamber may include a compressor.

A pressure tank may be fluidly connected with the compressor.

A valve or valves may be fluidly connected with one or more of the compressor, the pressure tank, and the expansion chamber for controlling the rate at which the expansion chamber expands and contracts, such as based on the blood flow requirements of a heart which is being assisted by the inventive device.

A control may be provided for varying the pumping rate of the pump or compressor.

The expansion chamber may include one or more lobes or fingers that draw in liquid and are filled with liquid as the expansion chamber expands, and which evacuate or expel liquid, such as blood, as the expansion chamber contracts or returns to its unexpanded state.

The lobe(s) or finger(s) are configured for sufficiently evacuating the fluid being transferred or pumped so that the expansion chamber is automatically continually cleaned; e.g., the fluid in all areas or regions of the expansion chamber is continually replaced and removed with newly drawn in fluid.

Relative terms such as left, right, first, second, up, and down are for convenience only and are not intended to be limiting.

DETAILED DESCRIPTION OF THE INVENTION

Figure 1:
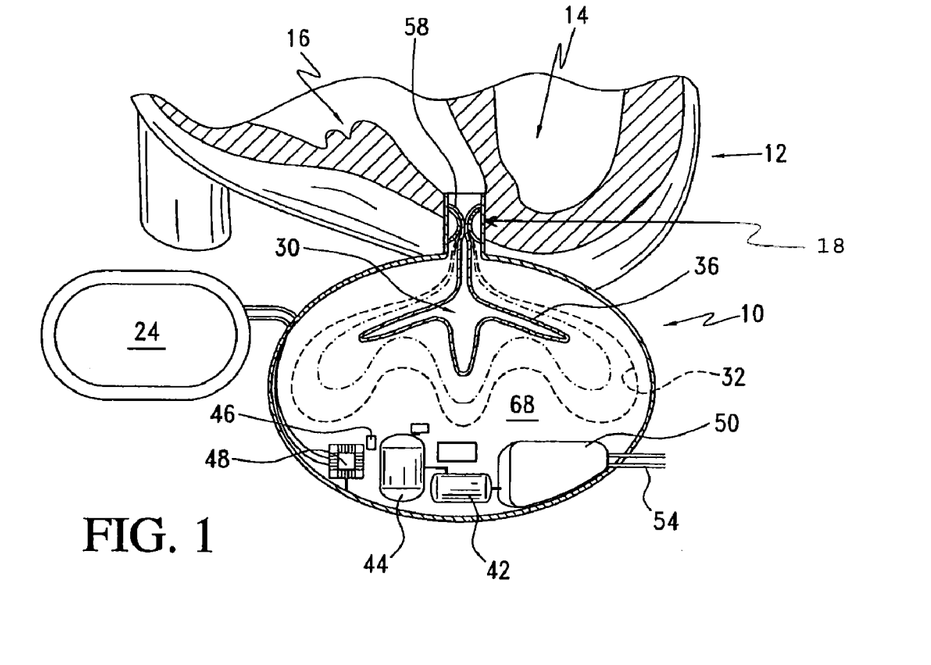
FIG. 1 is a schematic cross sectional view of a fluid transfer device, such as a ventricular assist device, fluidly connected to the right ventricle of a heart for assisting in pumping blood through the heart.

FIG. 1 shows a fluid transfer device or pump according to the invention, in use as a ventricular assist device (VAD) 10.

VAD 10 of FIG. 1 is shown in use on a heart 12 having a left ventricle 14 and a right ventricle 16. VAD 10 is shown in use as a right ventricular assist device (RVAD), shown fluidly connected to the right ventricle 16 of the heart.

VAD 10 may be provided with a housing 14, which may be substantially rigid. Housing 14 may be made of a material selected for a compatibility with tissue.

The fluid connection of RVAD 10 to the heart may be made with a connector 18 compatible with heart tissue, such connectors 18 being known.

A pacemaker control 24 for an RVAD may be used for controlling the timing of the RVAD in conjunction with the beating of the heart, as will be described further below.

An expansion chamber 30 having an expanded state 32 and an unexpanded state or mode 36 may be provided within housing 14. In expanded state or mode 32 the expansion chamber will be substantially filled with blood and in the unexpanded or resting state 36 the expansion chamber may be substantially empty.

A compressor or pump 42, such as an electric vacuum pump, may be provided for pressurizing a pressure tank 44 by pumping a fluid, such as a gas into pressure tank 44. A valve 46, which may be controlled by the pacemaker control 24 and associated control(s), such as an integrated chip 48 or other electronic controls, as will be readily understood, may serve to regulate the flow of the fluid located in the interior 48 of the housing for controlling the expansion and contraction of the expansion chamber 30.

A power source 50, such as a battery contained within housing 14, or an external battery or pneumatic or vacuum supply, may be used to power compressor 42. Alternatively, an externally controlled and operated vacuum and vent source may be used to expand and contract the chamber 30.

Battery 50 may be externally recharged via a body port connection 54.

Expansion chamber 30 may have one or more lobe-shaped or finger-like extensions. Three(3) finger-like extensions are shown. One opening 58 of expansion chamber 30 may be fluidly connected with connector 18 and, thus, fluidly connected to the user's heart.

In use compressor 42 draws in fluid, such as gas, contained in interior 48 of the housing, compresses the fluid, and forces the fluid into tank 44, as will be readily appreciated. In this manner, as the amount of gas in interior 68 is reduced, the pressure on the exterior of expansion chamber 30 is reduced, and expansion chamber 30 expands to its expanded condition 32, thereby drawing blood into expansion chamber 30. At the appropriate time as dictated by the heart beat, control 24 causes blood to be discharged from expansion chamber 30 through hole or fluid connection 58 synchronous with the discharging of the heart chamber. The blood is discharged by opening valve 46 fluidly connected to tank 44, thereby releasing pressurized gas from tank 44, refilling interior 48, thus raising the pressure therein, and causing expansion chamber 30 to return to its unexpanded state 36. The expansion chamber may be configured so that its natural state is unexpanded state 36, the elasticity of the material of expansion chamber assisting/causing the expansion chamber to return to its unexpanded state 36. In this manner, the expansion chamber returns to its unexpanded state should there by an unwarranted interruption in the operation of the VAD, such as in the case of a power failure.

Quite simply, the timing of the valve may be controlled by a known sense/pace pacemaker. The rate may automatically adjust discharge valve firing as needed. This may be termed a "pulsatile" type device.

The tank may be at atmospheric pressure so that there would not be a positive pressure within the user's body greater than atmospheric, in use.

As shown, RVAD 10 may be used without an artificial valve in conjunction with the natural valves of the heart, and need only be connected in one place on the heart, as appropriate, with known connective material. Beating (pumping) in sequence with the normal rate of the heart as fired by the pacemaker that senses heart rate change varies the operation of the compressor and/or the valve accordingly.

Figure 2:
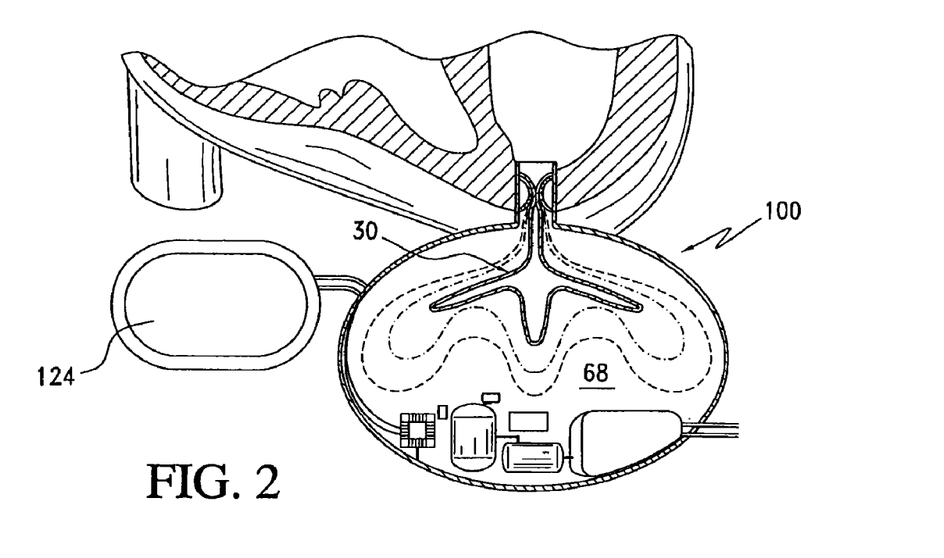
FIG. 2 is a schematic cross sectional view of fluid transfer device, such as a ventricular assist device, fluidly connected to the left ventricle of a heart for assisting in pumping blood through the heart.

FIG. 2 illustrates a left ventricular assist device (LVAD) 100 controlled by a pacemaker 124, and other controls depending on the configuration of the like components.

Figure 3:
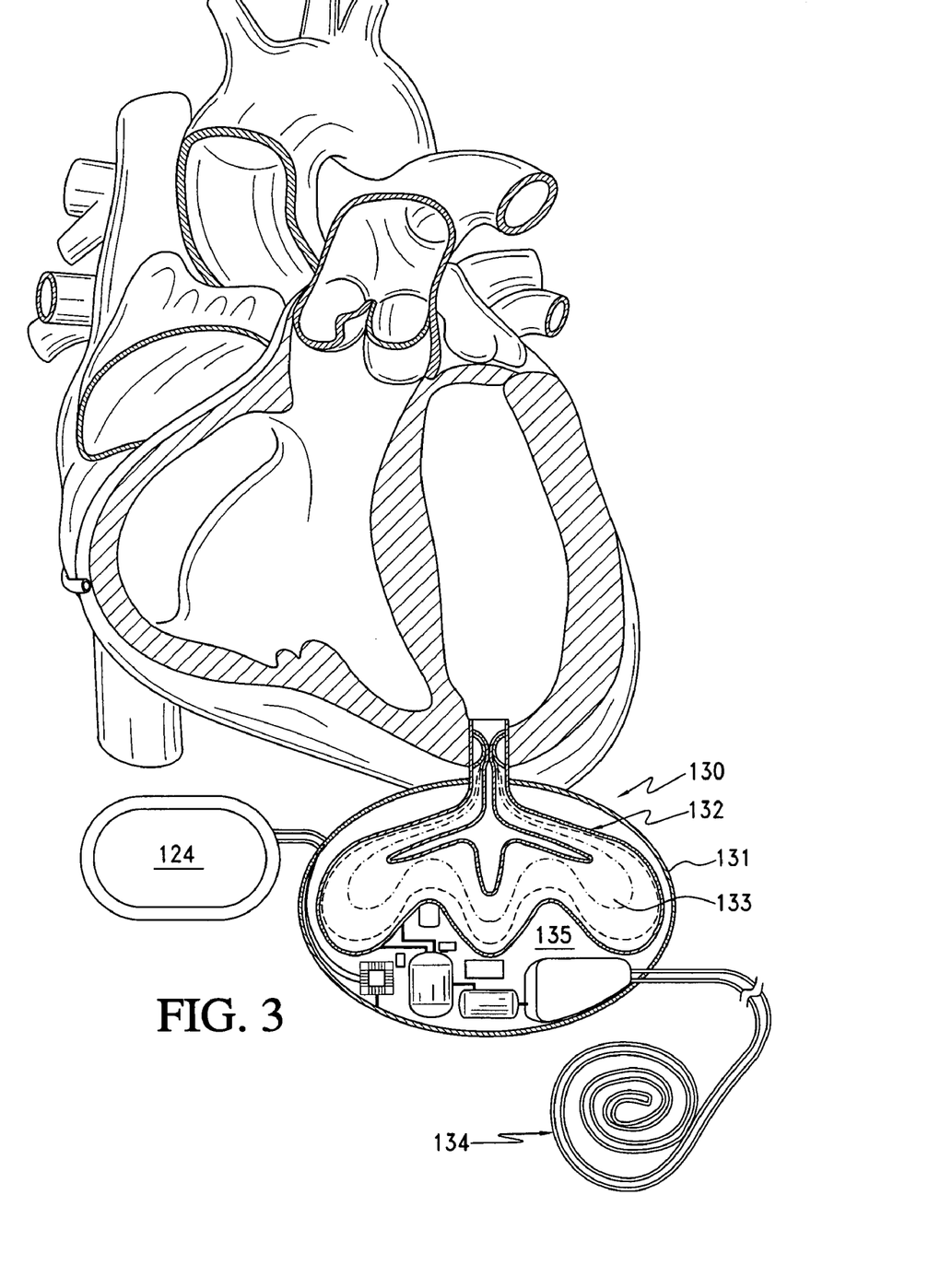
FIG. 3 is schematic cross sectional view of a further fluid transfer device, such as a ventricular assist device, shown fluidly connected to a ventricle of a heart for assisting in pumping blood through the heart.

FIG. 3 is schematic cross sectional view of a further fluid transfer device 130, such as a ventricular assist device, shown fluidly connected to a ventricle of a heart for assisting in pumping blood through the heart.

Cardiac assist device 130 is similar to the embodiment of FIGS. 1 and 2, with the addition of a further cavity 132 within housing 131. Further cavity 132 may be used to divide the interior of housing 131 into an inner cavity 133 and an outer cavity 135. As shown and described in greater detail with reference to FIGS. 4 and 5, wall 132 defining inner cavity 133 may include one or more curved regions 138, 142, and 144. Regions 138, 142, and 144 may be disclosed and configured for receiving expandable chamber or bladder 30 in its expanded conditions. For example, lobes or fingers or extensions 158, 162, and 164 may expand into the regions defined by respective ones of portions 138, 142, and 144.

In use, chamber 30 need not expand into contact with the inner wall of chamber 132. However, 132 may be configured so as to control expansion of chamber 30, as needed, in use.

Figure 4:
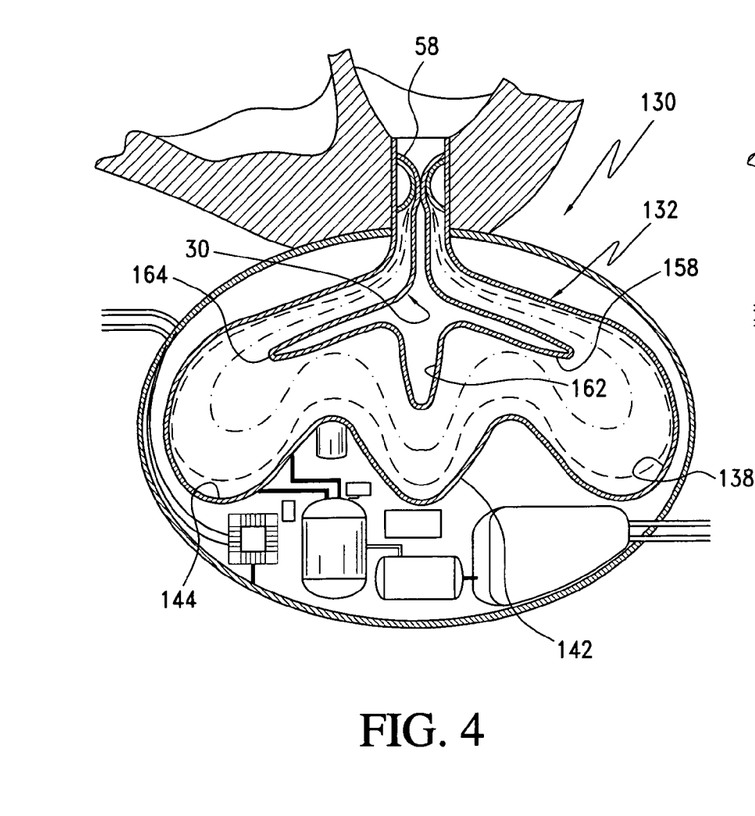
FIGS. 4 and 5 show the embodiment of FIG. 3, in use.

FIG. 4 shows chamber or bladder 30 in an unexpanded condition at atmospheric pressure with valve 58 in a closed position.

Figure 5:
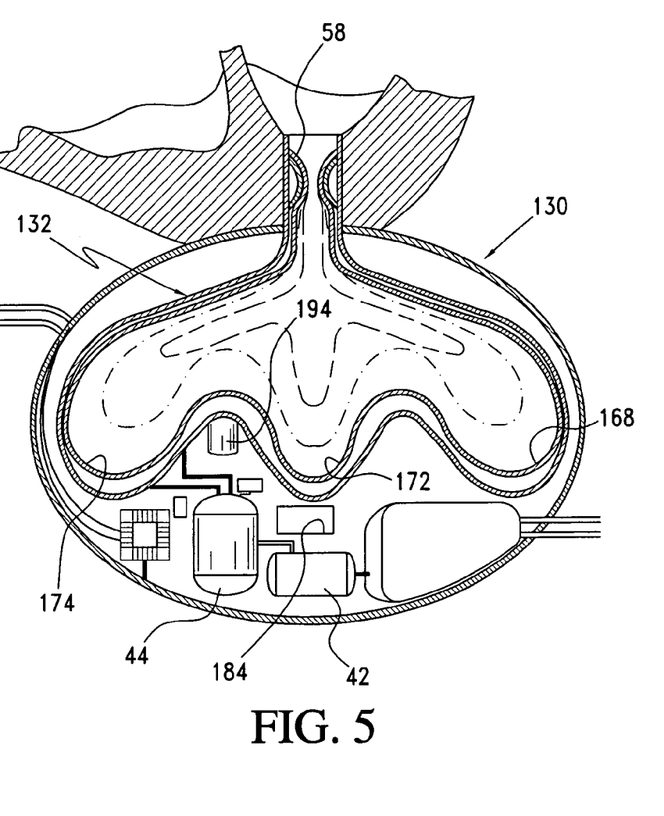

FIG. 5 shows chamber 30 in what may be termed a fully expanded condition having fully expanded lobes 168, 172, and 174 corresponding to respective ones of unexpanded lobes 158, 162, and 164.

Appropriate controls, such as a pacemaker, dedicated control chip, and the like may be provided as will be readily understood. For example, one or more valves 184 may be provided for controlling the accumulation and release of a fluid into and from pressure tank 44 into and from the inner cavity 133 for assisting in the expansion and contraction of chamber 30.

Quite simply, as in the previous embodiment, pump 42 may force a fluid provided in interior 133 in between the exterior of chamber 30 and the lobed inner wall 132 for developing a pressure less than atmospheric pressure within cavity 133; i.e. for developing a vacuum therein and, thus, causing chamber 30 to expand and draw in blood from the portion of the heart to which the device 130 is attached, in use. Then, when the drawn in blood is to be sent back into the heart for assisting in the pumping of blood in a patient, for example, valve 184 is open to allow release of fluid from pressure tank 44, to pressurize fluid exiting through valve 44 and fill and pressurizing cavity 133 so that, with the assistance of atmospheric pressure, the blood is forced out of expansion chamber 30 into the heart, in use. Pacemaker 124 and other appropriate controls will govern the expansion and contraction of chamber 30, as will be readily understood.

FIGS. 4 and 5 show the embodiment of FIG. 3, in use.

Figure 6:
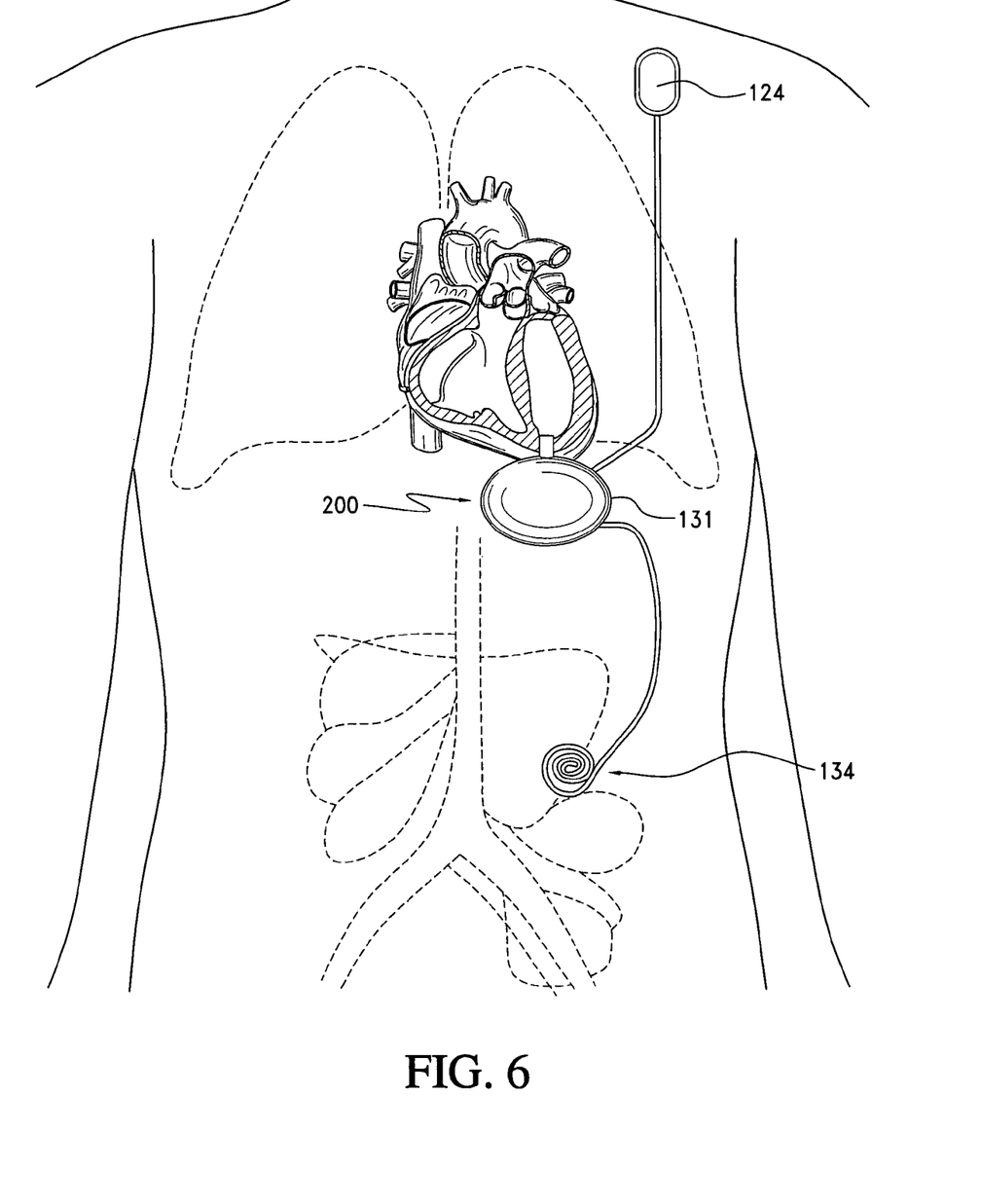
FIG. 6 is a schematic cross sectional view of another fluid transfer device according to the invention similar to FIG. 3 shown fluidly connected to a ventricle of a heart for assisting in the pumping of blood through the heart.

FIG. 6 is a schematic cross sectional view of another fluid transfer device 200 according to the invention similar to FIG. 3 shown fluidly connected to a ventricle of a heart for assisting in the pumping of blood through the heart.

Cardiac assist device 200, shown in use as a ventricular assist device, is similar to the embodiments of FIGS. 3-5. Cardiac assist device 200 may include recharger 134 for recharging a battery for powering device 200, recharger 134 being at a location remote from housing 131.

Likewise, pacemaker 124 may be located at a location distant from housing 134, as shown in FIG. 6, as will be readily appreciated.

Figure 7:
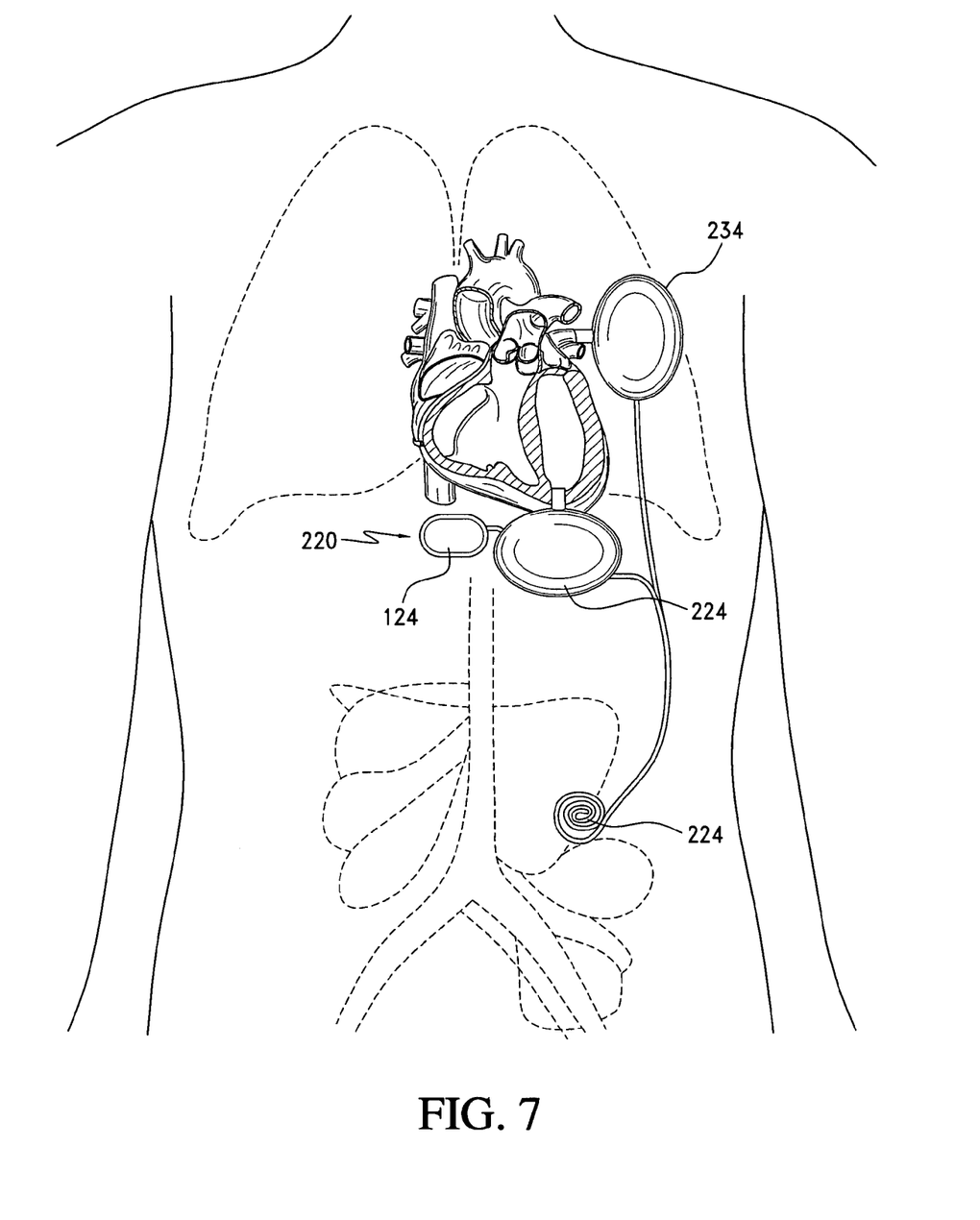
FIG. 7 is a schematic cross sectional view of another fluid transfer device according to the invention shown fluidly connected to both a ventricle and the aorta of a heart for assisting in the pumping of blood through the heart.

FIG. 7 is a schematic cross sectional view of another fluid transfer device 220 according to the invention shown fluidly connected to both a ventricle and the aorta of a heart for assisting in the pumping of blood through the heart.

Fluid transfer device 220 may be used for patients requiring both a ventricular assist device 224 and an aortic assist device 234.

Pacemaker 124 may be used to govern the operation, along with appropriate controls, as will be readily understood. Likewise, recharger 134, shown in a remote location, may be used to recharge a battery used for powering both devices, or for recharging respective batteries found in each one of ventricular assist device 224 and aortic assist device 234.

Figure 8:
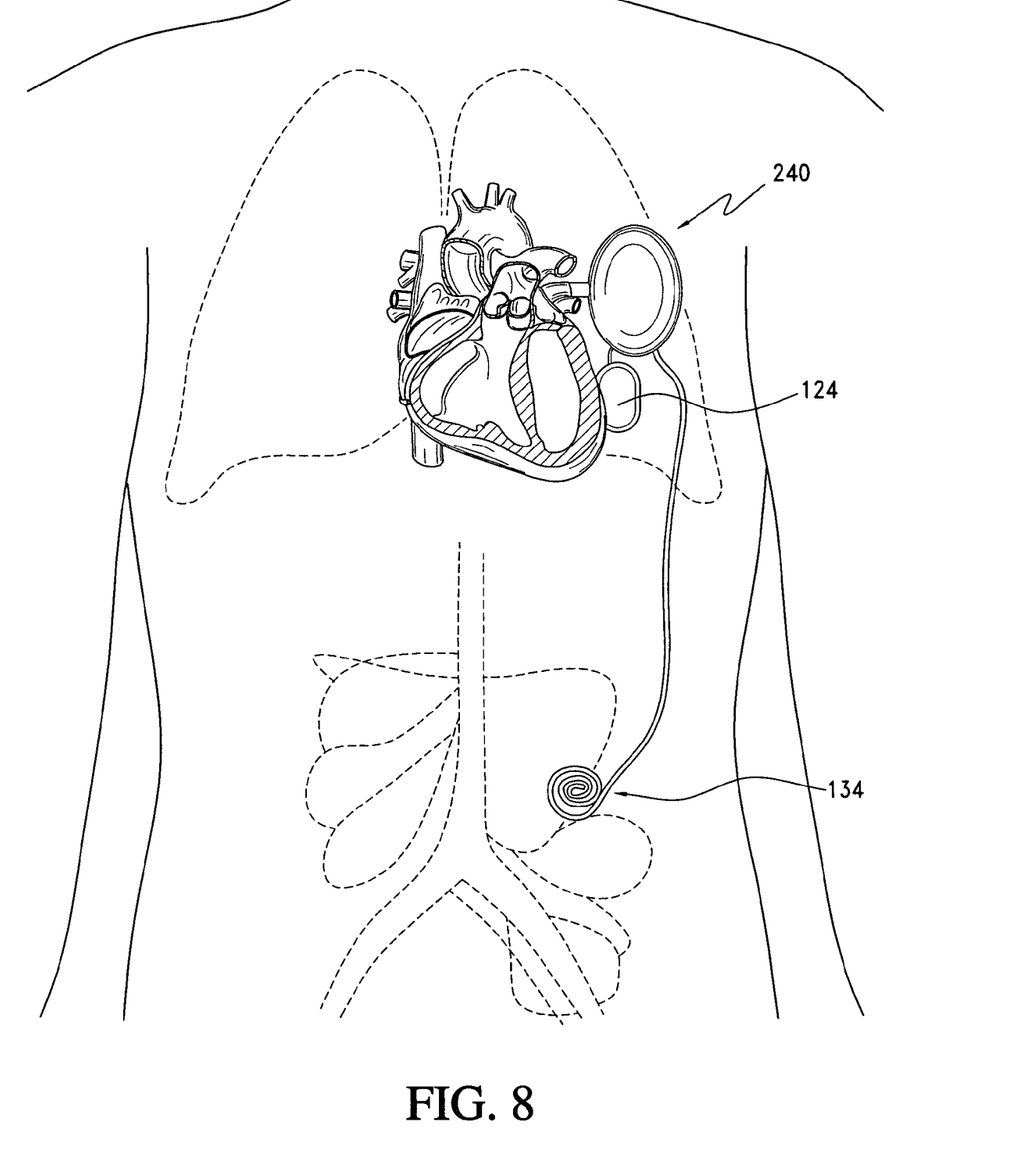
FIG. 8 is a schematic cross sectional view of another fluid transfer device according to the invention shown fluidly connected to the aorta of a heart for assisting in the pumping of blood through the heart.

FIG. 8 is a schematic cross sectional view of another fluid transfer device 240 according to the invention shown fluidly connected to the aorta of a heart for assisting in the pumping of blood through the heart.

Device 240 of FIG. 8 may be used as an aortic assist device 240, as shown. Pacemaker 124 may be used for controlling operation, and recharger 134 may be used for recharging an implanted battery housed within the casing of aortic assist device 240, as will be readily understood. Appropriate controls may be located within the housing of aortic assist device 240, outside the housing, and fully implanted, as patient requirements dictate, as in the other embodiments.

Figures 9, 10:
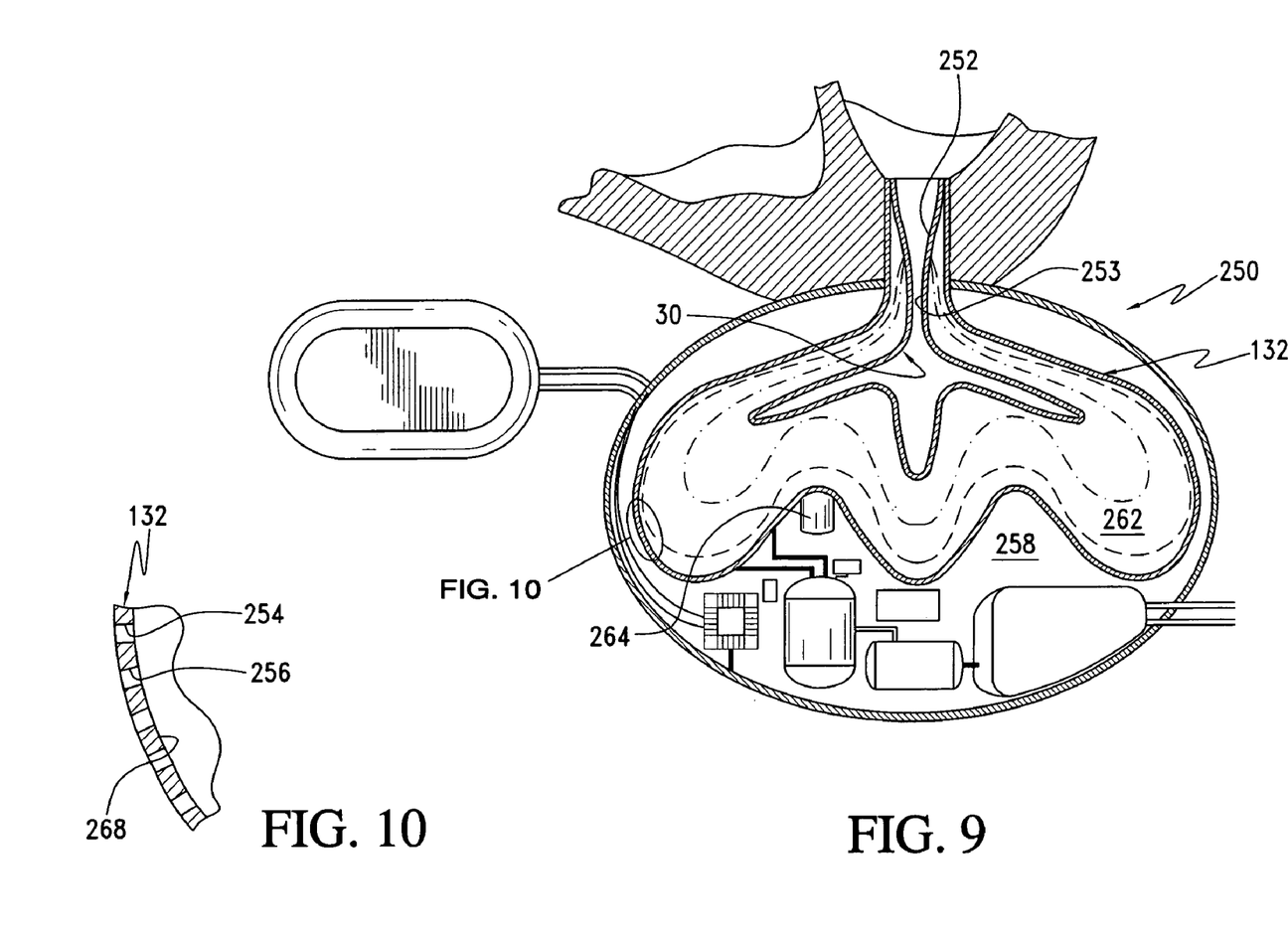
FIG. 9 is a schematic cross sectional view of another fluid transfer device according to the invention shown fluidly connected to a portion of a heart for assisting in the pumping of blood through the heart.
FIG. 10 is a partial cross sectional view of the fluid transfer device of FIG. 9.

FIG. 9 is a schematic cross sectional view of another fluid transfer device 250 according to the invention shown fluidly connected to a portion of a heart for assisting in the pumping of blood through the heart.

Fluid transfer device 250 may be termed a ventricular assist device, as it is shown connected to a ventricle of a patient's heart, as in other embodiments described herein.

Ventricular assist device 250 may include an opening or fluid connection 252 having no valve. Thanks to the configuration of expandable chamber or bladder 30 and the configuration of fluid connection 252, sufficient blood which had been drawn into the interior of chamber 30 during the expansion of chamber 30 will be exited or pushed out of the interior of chamber 30 under the influence of the pressurized fluid in the pressure tank and the pressure exerted by atmospheric pressure so that substantially no stagnant blood will remain within chamber 30. In other words, sufficiently little stagnant blood will remain in chamber 30 so as to lead to clotting. It is likewise contemplated that in a region 253, such as the illustrated narrowing region 253 of bladder 30, the bladder or expandable chamber 30 may be configured so that in its unexpanded condition, narrowed portion 253 completely closes and functions as a valve. In that manner, no additional valve need be used in the region of fluid connection 252.

FIG. 10 is a partial cross sectional view of the fluid transfer device of FIG. 9.

The wall or inner housing defining inner cavity 133 may be provided with one or more throughholes or perforations 254 and 256. A plurality of perforations 254 and 256 may be used to ensure that chamber 30 is expanded evenly, and to reduce the likelihood that a portion of chamber 30 might block a single hole, in use. In this manner, the negative pressure developed by the pump may be developed in an inner volume 258 for thus developing a negative pressure within the inner volume 262 defined within lobed wall 132 defining a lobed cavity and outside of lobed expandable chamber 30.

As in other embodiments of the invention, a sensor may be provided for determining whether or not there is a fluid leak within cavity 262; i.e. a fluid leak which might correspond to fluid leaking out of expandable chamber 30, in use. In the case of ventricular assist device 250, sensor 264, may sense the presence of leaked blood. Sensor 264 may sense the presence of blood by the use of a photosensor detecting a change in light or color within cavity 262 in the presence of blood. Sensor 264 may also include a moisture sensor or hygrometer for detecting a change in moisture content or relative humidity corresponding to the presence of a leaked fluid. Still further, sensor 264 may include a chemical sensor detecting the presence of a chemical or change in chemical composition. Sensor 264 may likewise include an electrical sensor for detecting a change in electrical resistance, for example. These are merely examples and are not intended to be limiting.

In this manner, an inner wall 268 may be treated or coated with a chemical for indicating the presence of a leak, such as by a change in chemical properties which may be detected by sensor 264.

Figure 11:
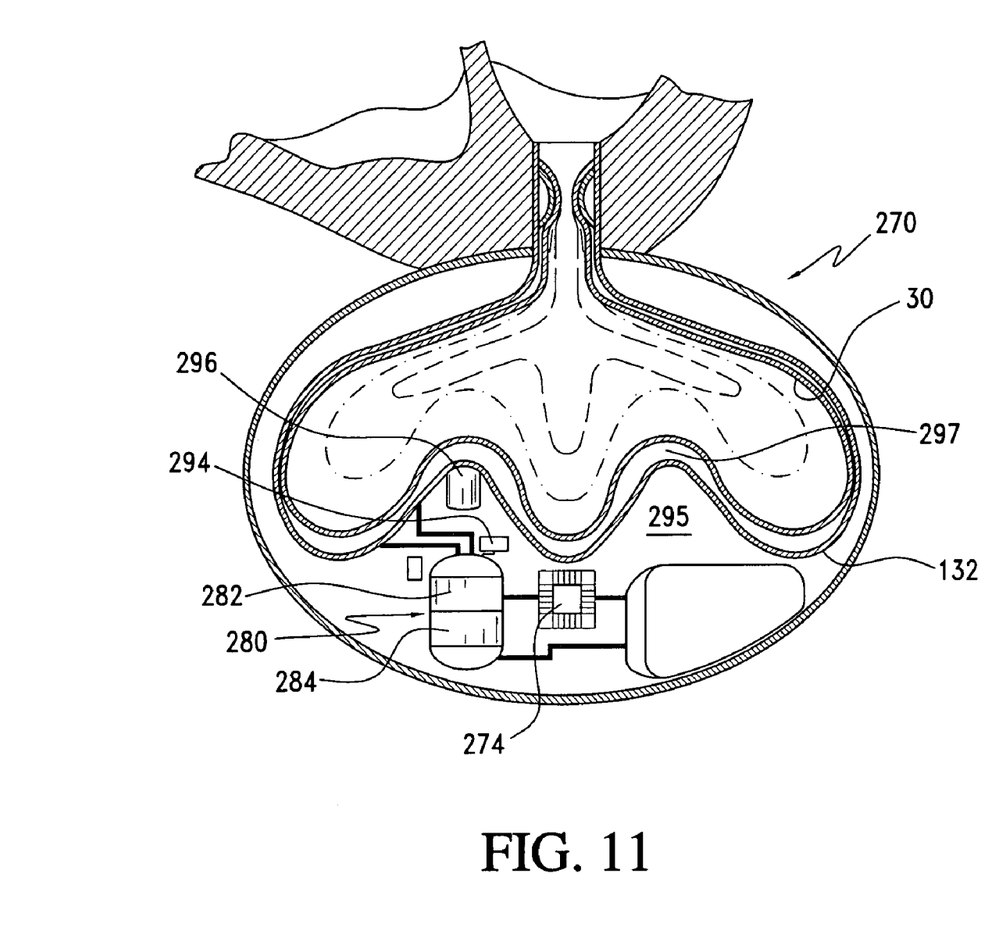
FIG. 11 is a schematic cross sectional view of another fluid transfer device according to the invention that requires no pacemaker and is shown fluidly connected to a portion of a heart for assisting in the pumping of blood through the heart.

FIG. 11 is a schematic cross sectional view of another fluid transfer device according to the invention that requires no pacemaker and is shown fluidly connected to a portion of a heart for assisting in the pumping of blood through the heart.

Device 270 of FIG. 11 may be used as a ventricular assist device, as shown. Device 270 may be particularly suited for compact or fully implanted situations. Device 270 may include a combined compressor and pressure tank or accumulator 280. Combination compressor and pressure tank 280 may include a pump or compressor 282 in one portion and a pressure tank 284 in another portion.

Controls, such as an electronic control, may be provided.

A valve 294 may fluidly connect compressor 282 pressure tank 284, and inner cavity 295, for example.

A perforated wall 132, as shown in FIGS. 10, may be provided so that the development of a vacuum in cavity 295 may serve to develop a respective vacuum in cavity 297 for expanding expandable chamber 30, along the lines described above.

To further reduce size requirements, a sensor 296, such as a pressure sensor, may be provided that is configured to substitute for the use of a pacemaker. Pressure sensor 296 may be configured to sense an increase in the blood pressure within a patient's heart, in use, so that thanks to control 274, the overall combination of elements will serve to function in concert with the pumping of the heart to assist in such pumping. Thanks to the use of an appropriate pressure sensor which detects changes in pressure transmitted through the fluid connection between the heart and pressure sensor 296, such fluid connection including the fluid (i.e. the blood) within chamber 30 and the fluid within cavity 297, it can be readily determined at which points in time the control 274 should cause the compressor to evacuate cavity 295 and, hence, lower the pressure below atmospheric pressure, for drawing blood into chamber 30 by the expansion of chamber 30, for example. Such pressure sensors and timing would be readily understood.

Figure 12:
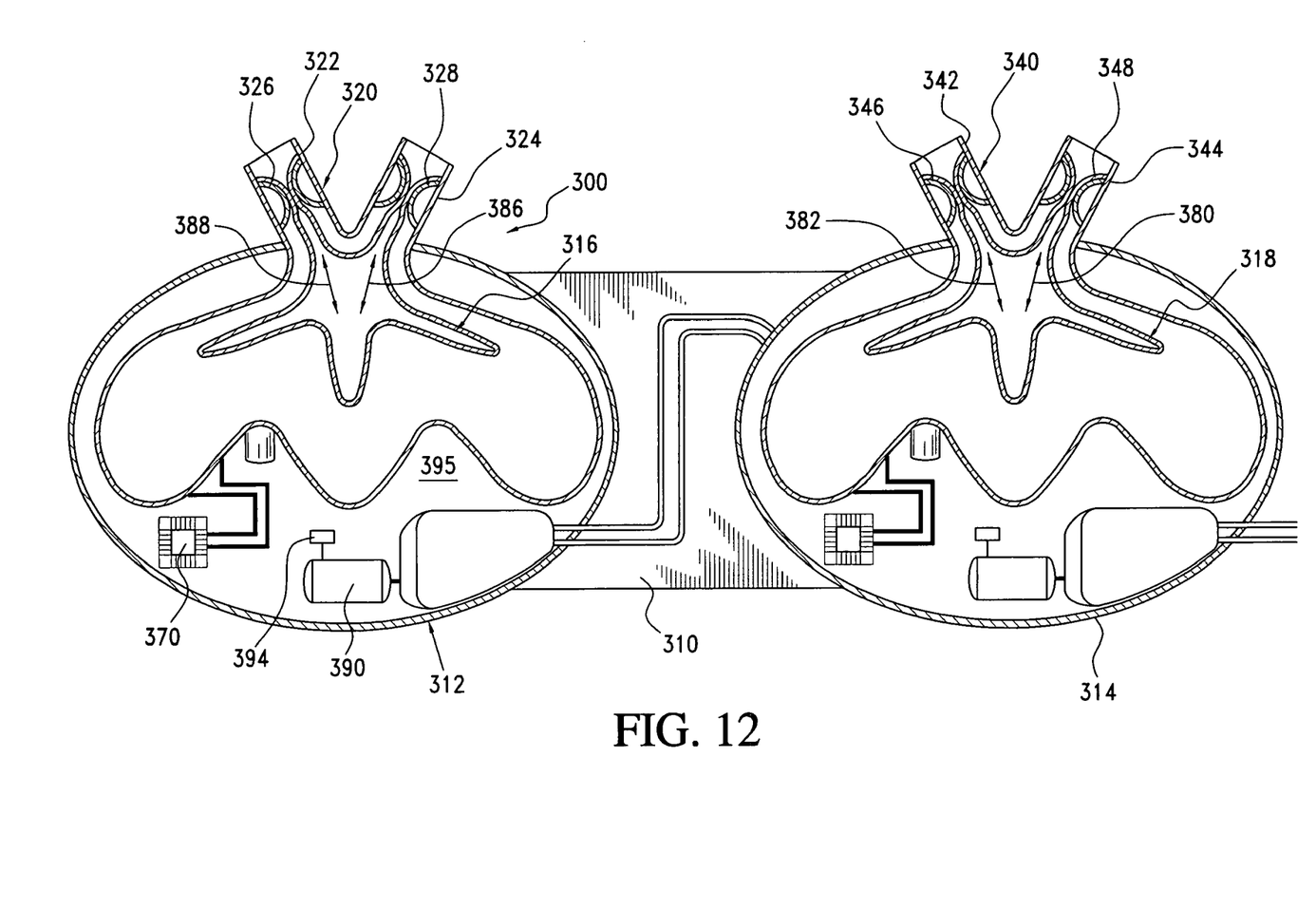
FIG. 12 illustrates another embodiment of a fluid transfer device, such as an artificial heart, shown with four valves for use in complete heart replacement.

FIG. 12 illustrates another embodiment of a fluid transfer device, such as an artificial heart, shown with four valves for use in complete heart replacement.

Fluid transfer device 300 may be used as an artificial heart 300, as shown. Artificial heart 300 may include a housing 310 including a first subhousing 312 and a second subhousing 314. First and second expandable lobed chambers 316 and 318 may be provided in respective housings 312 and 314.

A first fluid connection 320 may be provided for fluidly connecting chamber 316 with the exterior of cavity 312. First fluid connection 320 may include respective right and left fluid connections 322 and 324, each having respective left and right fluid valves 326 and 328.

In a similar manner, lobed chamber 318 may include a fluid connection 340 including left and right fluid connections 342 and 344, each such fluid connections 342 and 344 having respective left and right valves 346 and 348.

In use, fluid flow would be in respective directions represented by arrows 380, 382, 386 and 388, governed by controls 370 which dictate the manner in which respective valves 324, 326, 346, and 348 are opened and closed. As will be readily appreciated, depending on the manner in which artificial heart 300 is attached to a patient's veins and arteries (e.g., at which ones of fluid connections 322,324,344, and 344) the artificial heart recipient's veins and arteries are being attached, one or more of valves 326, 328, 346, and 348 may be actively controlled by control 370. One or more of the valves may be controlled by the expansion of chambers 316 and 318, depending on the intended use.

To enhance compactness, one or more combined compressors and pressure tanks 390 may be used; or, the pump 390 may be used and associated valve 394 so that interior 395 of subhousing 312 may be used as the pressure tank, as described in connection with other embodiments. It will be appreciated that the various controls may be used as in the other embodiments.

Any of the embodiments may be monitored from outside a patient's body, in use.

Any of the embodiments may be provided with variable pumping rates and volumes, pulsatile pumping, and other fine-tuning of the pumping of blood, in use, in order to enhance the operation of any of the embodiments, and so that any of the embodiments may be used for children so that the rate may be varied as they grow in stature, and for adult patients, so that the heart pressure and volume and rate may be increased as the patient convalesces, as deemed necessary.

It is further contemplated that any of the embodiments appropriate coatings may be provided on any of the interior and exterior of the expandable chambers and/or on the interior of the rigid housing or rigid lobed wall defining an outermost extent of the expansion chamber so as to eliminate platelet accumulation, reduced sheer, indicate fluid leaks, and enhance compatibility, and the like.

Any of the embodiments may be configured to minimize the surface area of the expandable chamber so as to minimize the surfaces on which platelets may accumulate, in the case where embodiments are used as cardiac assist devices or for pumping blood.

Any of the embodiments may be configured to minimize the stagnant (i.e. unpumped) volume of the material being pumped.

A pacemaker may be eliminated in respective embodiments, depending on the intended use.

In any of the embodiments by the use of atmospheric pressure to discharge the fluid there is a reduced likelihood that gas will permeate the fluid being pumped, as has been the case in prior art gas-filled systems.

It will be appreciated that devices in accordance with the invention may be used to replace entire chambers of the heart with the use of artificial inlet and outlet valves, as required.

It is further contemplated that two(2) of these fluid transfer devices or pumps according to the invention, along with artificial heart valves, as required may be used to completely replace a patient's heart.

The pump may be located outside the body and used to pump blood.

In the case of children or certain conditions, the valve may be partially open during the compression stage.

Additional control(s), such as a dedicated chip, may be provided.

One or more of the pump, compressor, pressure tank, battery, battery charger, controls, and the like may be located inside the housing, outside the housing and inside the patient's body, and/or outside of the patient's body, depending on patient requirements, for example, and other considerations.

While this invention has been described as having a preferred design, it is understood that it is capable of further modifications, and uses and/or adaptations of the invention and including such departures from the present disclosure as come within the known or customary practice in the art to which the invention pertains, and as may be applied to the central features hereinbefore set forth, and as fall within the scope of the invention.

The invention claimed is:

1. A fluid transfer device comprising:
a housing having a cavity therein;
an expandable lobed chamber provided in the cavity;
a connector for fluidly connecting an interior of the expandable lobed chamber and a source of a fluid external to the housing, the connector being adapted to convey both an influx of the fluid into the expandable lobed chamber and an outflow of the fluid from the expandable lobed chamber;
a pump provided in the cavity to establish a negative pressure sufficiently great to cause the expandable lobed chamber to expand into an expanded condition;
the housing being configured to be fully implanted in a patient and sufficiently strong to withstand the negative pressure between an exterior of the lobed chamber and within the cavity sufficiently great to cause the lobed chamber to expand into the expanded condition and draw the fluid through the connector from external to the housing into the interior of the lobed chamber when the negative pressure is established in the cavity; and
the lobed chamber being configured so that the lobed chamber is in a substantially empty unexpanded condition when the cavity and, hence, the lobed chamber is at atmospheric pressure.

2. The fluid transfer device as in claim 1, wherein:
the expandable lobed chamber includes at least two lobes.

3. The fluid transfer device as in claim 1, wherein:
the expandable lobed chamber includes at least three lobes.

4. The fluid transfer devices as in claim 1, wherein:
the housing is configured for use as a ventricular assist device; and
the connector is configured for being fluidly connected to the interior of a ventricle of the patient's heart.

5. The fluid transfer device as in claim 4, wherein:
in the expanded condition and the unexpanded condition blood is sufficiently drawn into and discharged, respectively, from the lobed chamber, in use, so that insufficient platelet accumulation occurs to cause clotting of blood in the lobed chamber, in use.

6. The fluid transfer device as in claim 5, wherein:
the unexpanded condition of the lobed chamber is sized and configured so that there is substantially no stagnant fluid volume in the lobed chamber in the unexpanded condition, in use.

7. The fluid transfer device as in claim 1, wherein:
a battery is provided in the housing, the battery being operatively connected to the pump.

8. The fluid transfer device as in claim 7, wherein:
the battery is rechargeable by a battery charger located externally of the patient's body, in use.

9. The fluid transfer device as in claim 1, wherein:
a control is provided and operatively associated with the pump; and
wherein the control is configured for dynamically controlling at least one of rate and volume and hence the expansion and contraction of the chamber into its respective expanded and unexpanded conditions in response to a heart rate.

10. The fluid transfer device as in claim 1, wherein:
the housing is configured for being fully implanted within the patient's torso, in use.

11. The fluid transfer device as in claim 1, wherein:
a valve is provided in the connector for opening and closing a fluid connection between the source of the fluid external to the housing and the interior of the chamber, in use.

12. The fluid transfer device as in claim 11, wherein:
the connector is configured for being fluidly connected to the aorta of the patient's heart, in use.

13. The fluid transfer device as in claim 11, wherein:
the connector is configured for being connected to a ventricle of the patient's heart, in use; and
a further housing having a further cavity is provided;
a further expandable lobed chamber is provided in the further cavity of the further housing;
a further connector is provided for fluidly connecting a further source of the fluid external to the further housing with the interior of the further expandable lobed chamber;
the further connector is configured for being fluidly connected to the aorta of the patient's heart, in use;
the further housing is configured to be fully implanted in a patient and sufficiently strong to withstand a negative pressure between an exterior of the further lobed chamber and within the further cavity sufficiently great to cause the further lobed chamber to expand into an expanded condition and draw the fluid through the fluid connection from the further source of the fluid external to the further housing into the interior of the further lobed chamber when a negative pressure is established in the further cavity; and
the further lobed chamber is configured so that the further lobed chamber is in a substantially empty unexpanded condition when the further cavity and, hence, the further lobed chamber is at atmospheric pressure.

14. The fluid transfer device as in claim 1, wherein:
the cavity includes first and second cavities;
the expandable lobed chamber includes first and second lobed chambers;
the connector includes first and second connectors;
the first connector includes first left and first right connectors;
the second connector includes second left and second right connectors;
a valve is provided in each one of the respective first left and first right connectors of the first connector and in each one of the respective second left and second right connectors of the second connector;
respective ones of the first and second left and right connectors are connectable to respective veins and arteries of the patient, when implanted in the patient, in use; and
a control is provided and operatively associated with respective ones of the pump and the valves to cause the fluid transfer device to function as an artificial heart.

15. The fluid transfer device as in claim 1, wherein:
a battery is provided in the housing for operating the pump.

16. The fluid transfer device as in claim 1, wherein:
the connector is configured for being connected to a portion of the patient's heart; and
a pressure sensor is operatively associated with the connector and configured for sensing a fluid pressure within the patient's heart, so that the device can be operated and function as a cardiac assist device without use of a pacemaker.

17. The fluid transfer device as in claim 1, wherein:
a pressure sensor is operatively associated with the cavity in the housing and is configured for sensing fluid pressure within the cavity for detecting fluid leaks into the cavity.

18. The fluid transfer device as in claim 1, wherein:

a sensor is operatively associated with the cavity in the housing and is configured for sensing a fluid leak within the cavity, the sensor including one of a photo-sensor; a chemical sensor, an electrical sensor, and a moisture sensor.

19. A fluid transfer device comprising:

a housing having a cavity therein;

an expandable lobed chamber provided in the cavity;

a fluid connection provided for fluidly connecting an interior of the expandable lobed chamber with a source of a fluid external to the housing; and a pump provided in the cavity to establish a negative pressure sufficiently great to cause the expandable lobed chamber to expand into an expanded condition;

the housing being configured to be fully implanted in a patient and sufficiently strong to withstand the negative pressure between an exterior of the lobed chamber and within the cavity sufficiently great to cause the lobed chamber to expand into the expanded condition and draw a fluid through the fluid connection from external to the housing into the interior of the lobed chamber when the negative pressure is established in the cavity;

the lobed chamber being configured so that the lobed chamber is in a substantially empty unexpanded condition when the cavity and, hence, the lobed chamber is at atmospheric pressure; and the fluid connection being adapted for use without a valve.

* * * * *